(12) United States Patent
Foerster

(10) Patent No.: US 8,303,591 B1
(45) Date of Patent: Nov. 6, 2012

(54) LOAD SHAPING FOR DYNAMIC TENSIONING MECHANISMS AND METHODS

(75) Inventor: Seth A. Foerster, San Clemente, CA (US)

(73) Assignee: Dallen Medical, Inc., San Clemente, CA (US)

( * ) Notice: Subject to any disclaimer, the term of this patent is extended or adjusted under 35 U.S.C. 154(b) by 656 days.

(21) Appl. No.: 12/406,904

(22) Filed: Mar. 18, 2009

Related U.S. Application Data

(60) Provisional application No. 61/037,582, filed on Mar. 18, 2008.

(51) Int. Cl.
*A61B 17/56* (2006.01)
(52) U.S. Cl. .......................................... 606/74; 606/326
(58) Field of Classification Search .................. 606/228, 606/232, 233, 139, 144, 145, 74, 103, 104, 606/151, 69, 72, 105
See application file for complete search history.

(56) References Cited

U.S. PATENT DOCUMENTS

| | | |
|---|---|---|
| 303,360 A | 8/1884 | Brunner |
| 3,822,445 A | 7/1974 | Feng |
| 4,279,248 A | 7/1981 | Gabbay |
| 4,444,181 A | 4/1984 | Wevers et al. |
| 4,535,772 A | 8/1985 | Sheehan |
| 4,667,675 A | 5/1987 | Davis |
| 4,730,615 A | 3/1988 | Sutherland et al. |
| 4,813,416 A | 3/1989 | Pollak et al. |
| 4,901,721 A | 2/1990 | Hakki |
| 4,938,760 A | 7/1990 | Burton et al. |
| 4,959,064 A | 9/1990 | Engelhardt |
| 4,969,892 A | 11/1990 | Burton et al. |
| 5,330,489 A | 7/1994 | Green et al. |
| 5,339,870 A * | 8/1994 | Green et al. ............... 140/123.5 |
| 5,366,461 A | 11/1994 | Blasnik |
| 5,571,105 A | 11/1996 | Gundolf |
| 5,722,976 A | 3/1998 | Brown |
| 5,797,915 A * | 8/1998 | Pierson et al. .................. 606/74 |
| 5,807,214 A | 9/1998 | Riazi |
| 5,810,854 A | 9/1998 | Beach |
| 5,849,012 A | 12/1998 | Abboudi |
| 5,972,006 A | 10/1999 | Sciaino, Jr. |
| 6,051,007 A | 4/2000 | Hogendijk et al. |
| 6,066,160 A | 5/2000 | Colvin et al. |
| 6,080,185 A | 6/2000 | Johnson et al. |
| 6,471,715 B1 | 10/2002 | Weiss |

(Continued)

*Primary Examiner* — Thomas Barrett
*Assistant Examiner* — Melissa A Golob
(74) *Attorney, Agent, or Firm* — Stout, Uxa, Buyan & Mullins, LLP; Donald E. Stout

(57) ABSTRACT

A surgical tensioning device for dynamically holding two tissue portions in contact with one another comprises a resilient body having a plurality of spring elements, and a plurality of stop members for limiting travel of the spring elements in order to control energy stored or delivered by the spring elements. A length of suture is also provided, wherein a first end of the suture is connected to the resilient body at a first attachment point and a second end of the suture is connected to the resilient body at a second attachment point. In one embodiment, the stop members contact one another to limit compression of the spring elements. When the suture is placed in tension, the spring elements move to an extended configuration and the stop members move apart, creating gaps between ends of each of the stop members. When the gaps become sufficiently large, edges of the stop elements contact corresponding spring elements to impede further widening of the gaps and consequent further extension of the spring elements, thus protecting the springs.

29 Claims, 4 Drawing Sheets

U.S. PATENT DOCUMENTS

| | | |
|---|---|---|
| 6,540,769 B1 | 4/2003 | Miller, III |
| 6,547,725 B1 | 4/2003 | Paolitto et al. |
| 6,589,246 B1 | 7/2003 | Hack et al. |
| 6,648,903 B1 | 11/2003 | Pierson, III |
| 6,969,398 B2 | 11/2005 | Stevens et al. |
| 6,997,189 B2 | 2/2006 | Biggs et al. |
| 7,108,710 B2 | 9/2006 | Anderson |
| 7,341,558 B2 | 3/2008 | de la Torre et al. |
| 7,416,556 B2 | 8/2008 | Jackson |
| 7,722,632 B2 | 5/2010 | Rothstein et al. |
| 7,867,251 B2 | 1/2011 | Colleran et al. |
| 7,867,253 B2 | 1/2011 | McMichael et al. |
| 2002/0147449 A1 | 10/2002 | Yun |
| 2003/0093117 A1 | 5/2003 | Saadat |
| 2005/0075653 A1 | 4/2005 | Saadat et al. |
| 2005/0090827 A1 | 4/2005 | Gedebou |
| 2005/0149121 A1 | 7/2005 | Crombie et al. |
| 2005/0240203 A1 | 10/2005 | Fuseri et al. |
| 2005/0251209 A1 | 11/2005 | Saadat et al. |
| 2007/0073289 A1 | 3/2007 | Kwak et al. |
| 2007/0112385 A1 | 5/2007 | Conlon |
| 2007/0213725 A1 | 9/2007 | Hack |
| 2007/0276437 A1 | 11/2007 | Call et al. |
| 2007/0293863 A1 | 12/2007 | Reimels et al. |
| 2007/0293864 A1 * | 12/2007 | Reimels et al. .............. 606/69 |
| 2008/0004624 A1 | 1/2008 | Olroyd |
| 2008/0015589 A1 | 1/2008 | Hack |
| 2009/0062853 A1 | 3/2009 | McMichael et al. |

* cited by examiner

LOAD SHAPING FOR DYNAMIC TENSIONING MECHANISMS AND METHODS

This application claims the benefit under 35 U.S.C. 119(e) of the filing date of Provisional U.S. Application Ser. No. 61/037,582, entitled Dynamic Ring Compression Device, filed on Mar. 18, 2008, and expressly incorporated herein by reference, in its entirety. This application is also related to co-pending U.S. patent application Ser. No. 12/347,821, entitled Dynamic Suture Tensioning Device and filed on Dec. 31, 2008, and to U.S. Utility patent application Ser. No. 12/406,902, entitled Knotless Dynamic Suture Tensioning Device and Methods, and Ser. No. 12/406,909, entitled Dynamic Tissue Holding Device with Low Profile Spring, both filed on even date herewith, all of which are commonly assigned and expressly incorporated herein, by reference, in their entirety.

BACKGROUND OF THE INVENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote healing. Compression and stability are critical for proper anatomical healing of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

A common problem in using suture is the variable nature of the residual tension realized after the knot is tied. Hand tied knots usually supply only a fraction of the residual tension for which the suture is capable. There are various procedures where the residual tension in a hand tied knot is insufficient to approximate and generate the compression needed for healing between tissues. There are times when high tension may cause suture to cut into tissue at points of stress concentration. This suture cutting may not happen immediately. It can take place as the tissue degrades or relaxes, or sometimes there are external forces that cause the suture to cut into the tissue. This cutting action releases tension in the suture and adversely affects the quality and durability of the repair.

What is needed, therefore, are devices and techniques for holding two tissue portions in a state of compression and tension beyond that which is commonly achieved using hand-tied sutures.

SUMMARY OF THE INVENTION

The present invention solves the problems outlined above by providing a means to approximate two tissue portions together so that there is compression in the tissue interface. The invention provides a means to hold two tissues in a state of compression beyond that which is commonly achieved with the hand tying of sutures. The invention may also be used to lengthen retracted tendons or ligaments. This is done by anchoring one end of the suture on bone and the other end on tendon or a ligament. The dynamic tensioning element in the invention serves to stretch and optionally attach the tendon or ligament to the bone.

Attached to one end of the suture is a resilient mechanism designed to keep tension in the suture, as tissues will shrink during healing. This resilient mechanism lies on top of the tissues to be approximated. The free end of the suture is brought to the resilient mechanism and routed into an integral receptacle such that pulling on the suture end will bring the tissues together. As the tissues come together and tension is brought to the suture, the resilient mechanism will activate and start to store the energy needed to activate the resilient mechanism, in order to keep tension on the suture when the tissues shrink during healing.

The present invention employs springs used in the inventive resilient mechanisms to avoid overextension due to forces imparted by relatively stronger tissues such as bone or tendon. The inventive resilient mechanisms employ spring forces which are lower in order to optimize healing times and to avoid strangulation of tissues. Additionally, the springs employed in the inventive resilient mechanisms are protected by limiting mechanisms or stops in order to avoid handling failures.

Another feature of the innovative resilient mechanisms of the present invention is the avoidance of excessive latent friction in the suture lock mechanism, to avoid overloading the spring. The types of springs used in dynamic suture tensioning cannot supply a constant force as they travel inwardly. The specifications for optimum bone healing do fall in a range, but not the range supplied by the spring. This range is better approximated by preloading the spring. A spring preloading method utilized in the present invention is to extend the spring to a high energy state and then insert a stop that prevents the spring from fully returning to its natural state.

The tissue portions comprise biological tissue in the body, including, but not limited to, skin, tendon, bone, ligaments, blood vessels, and organs. The suture may comprise woven, braided, or knitted fibers or metals, or a monofilament, and can be made of any known suture material. The suture may be of any shape, including, but not limited to, round, square, oval, flat (like a strap), or tubular. The shape of the suture for particular embodiments will be discussed more fully hereinbelow.

More particularly, there is disclosed a surgical tensioning device for dynamically holding two tissue portions in contact with one another. The device comprises a resilient body having a plurality of spring elements, and a plurality of stop members for limiting travel of the spring elements in order to control energy stored or delivered by the spring elements. A length of suture is also provided, wherein a first end of the suture is connected to the resilient body at a first attachment point and a second end of the suture is connected to the resilient body at a second attachment point. Preferably, the suture comprises flat suture, and the spring elements comprise leaf springs. In one embodiment, the stop members contact one another to limit compression of the spring elements. When the suture is placed in tension, the spring elements move to an extended configuration and the stop members move apart, creating gaps between ends of each of the stop members. When the gaps become sufficiently large, edges of the stop elements contact corresponding spring elements to impede further widening of the gaps and consequent further extension of the spring elements.

In some embodiments, such as the one above described, the stop elements are formed of a relatively rigid material. In other embodiments, such as one which will be described below, the stop elements are formed of a relatively flexible material, and, more preferably, comprise relatively flexible straps.

In this second embodiment, one of the straps, disposed between the first and second attachment points, is substantially shorter than a corresponding one of the spring elements. Thus, the spring elements are prevented from further extension once the straps become fully extended between the first and second attachment points. The straps may be internal, or may extend externally to the spring elements. The external straps may be either flexible or rigid. A buckle may be provided for containing tension applied to one of the suture ends during tensioning.

In another aspect of the invention, there is disclosed a method for securing together two spaced bodily tissues using a cerclage procedure. The method comprises a step of wrapping a length of suture about the tissue to be secured together, wherein first and second ends of the suture are connected to attachment points on a resilient body. The resilient body is pre-compressed to apply tension to the suture ends, so that the tissue portions to be secured together are compressed together. As the tissues begin to heal, and tension is applied to the suture ends, as a result of the healing process, the extension of a spring element in the resilient body is limited. The limiting step is performed by engaging a stop against the spring element after a predetermined extension travel of the spring element. The stop may comprise a relatively rigid member which engages the spring element to inhibit further extension thereof, or it may comprise a strap which attains its full length when the spring element has traveled the predetermined extension distance, thereby preventing further extension of the spring element.

A further step of the method is a step of limiting the compression travel of the resilient body to avoid tissue strangulation.

The invention, together with additional features and advantages thereof, may best be understood by reference to the following description taken in conjunction with the accompanying illustrative drawings.

DESCRIPTION OF THE PREFERRED EMBODIMENT

Figure 1:
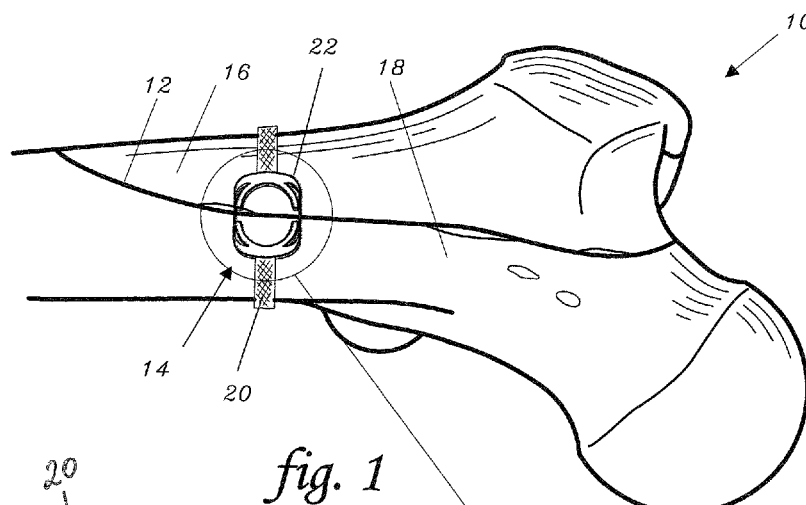
FIG. 1 is a plan view showing the broken head of a femur having a fracture being held together by a device constructed in accordance with the principles of the present invention.

Referring now more particularly to the drawings, there is shown in FIG. 1 the broken head of a femur 10 having a fracture 12. A cerclage device 14, constructed in accordance with the principles of the present invention, is deployed to hold bone fragments 16 and 18 together. The device 14, which comprises a tension band, is made up of a suture 20 and a resilient body 22. The tension band 14 is designed so that continuous tension is applied during the entire healing process. As the bone fragments 16 and 18 heal and attach to each other over time, the fragments 16 and 18 actually move and absorb into one another. As is desirable for optimal healing, the tension band 14 supplies the forces necessary to push bone fragments 16, 18 into one another. Optimal healing dictates that the initial forces imparted on the bone fragments are not as high as the physiologic or native load bearing forces that one would expect at the healing site. This imposes competing functions on the tensioning device 14 in its initial state. The present invention addresses this issue by providing a mechanism that interferes with the resilient function of the device 14 should excessive forces be realized.

As healing progresses, the resilient nature of the tensioning device 14 diminishes as springs 24 (FIGS. 1a and 1b) lose their energy to pulling the suture in, as bone fragments 16 and 18 move into one another. As the springs 24 lose their energy, the compression that they are able to impart on the bone fragments 16 and 18 diminishes. Optimal bone healing requires that some suture tension be maintained until the end of the healing cycle. Normally, a resilient mechanism decreases its rate of energy release until it approximates zero at the end of the cycle. This is not desired according to optimal healing parameters, but is desirable in that zero forces need to be realized at the end of the healing cycle in order to avoid strangulation of the tissue. The tensioning device 14 will otherwise start to act as a tourniquet and strangulate the tissue it just healed. Again, there are competing functions for the tensioning device 14. The present invention addresses this problem by pre-loading the resilient mechanism with the amount of minimum energy necessary to induce optimum healing.

Figure 1A:
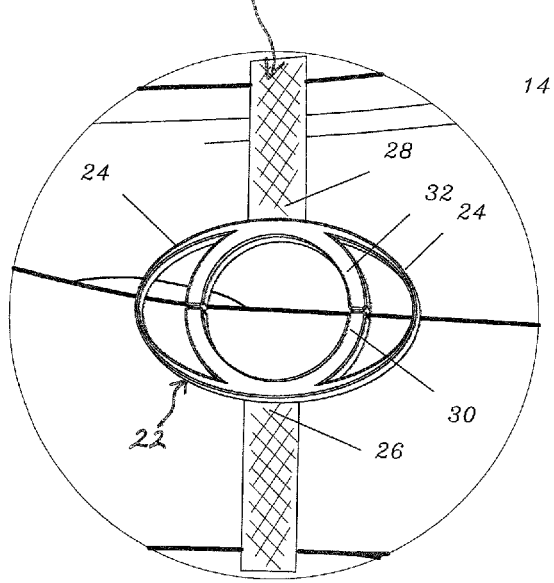
FIG. 1a is an enlarged detail view of the portion A of FIG. 1, illustrating the resilient body element of the inventive device in its initial state.

FIG. 1a shows the resilient body 22 in its initial state. The spring elements 24 may be compressing resilient body 22 such that a stop 30 is being pressed into another stop 32. This initial compression effectively preloads the resilient body 22 to ensure that tension is applied to the suture 20, which, in turn, compresses bone fragments 16 and 18 at the end of the healing cycle. But, because stops 30 and 32 come into contact with each other, tissue strangulation is avoided. Spring elements 24 within the resilient body 22 serve to pull on suture ends 26 and 28, thereby tensioning the suture 20, which acts to pull the bone fragments 16 and 18 together. The spring elements 24 are preferably leaf springs, and are designed to pull with the appropriate amount of tension to generate optimal compression in the fracture 12 so that the femur 10 will heal as quickly as possible.

Figure 1B:
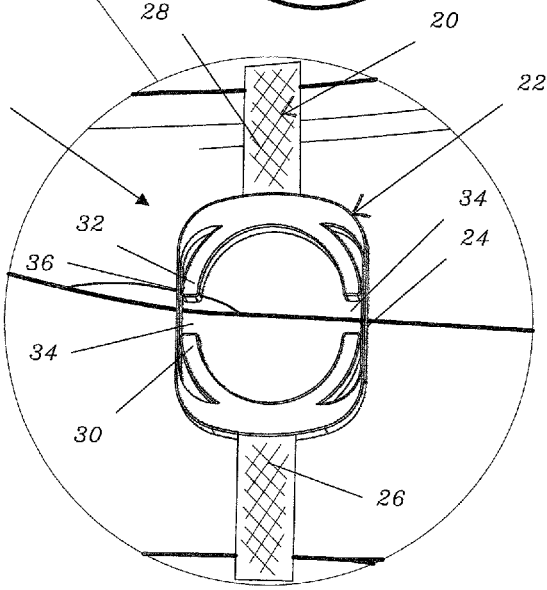
FIG. 1b is an enlarged detail view of the portion A of FIG. 1, similar to FIG. 1a, wherein the springs of the resilient body element are at full extension.

FIG. 1b shows the springs 24 in their full extension, storing all of the energy needed to serve the functions of the tensioning device 14. Loading springs 24 requires the tensioning of the suture ends 26 and 28 into the tensioning device 14, and then locking or binding suture ends 26 and 28 to tensioning device 14 as indicated. A gap 34 can be seen between stops 30 and 32, indicating the resilient mechanism has been loaded with energy. The gap 34 is also the distance to be traveled during the healing process. When the gap 34 widens, springs 24 interfere with the outwardly adjacent surface to stops 30 and 32. This dramatically impedes further widening of the gap 34 as the forces to do so increase at a much higher rate. The present invention enables this higher rate to be matched with expected physiologic or native load bearing forces.

The tensioning device 14 is now ready to provide compression between bone halves 16 and 18, while also providing greater resistance to expected physiologic or native load bearing forces, and while also terminating all compressive forces once the fracture 12 has fully healed.

Figure 2:
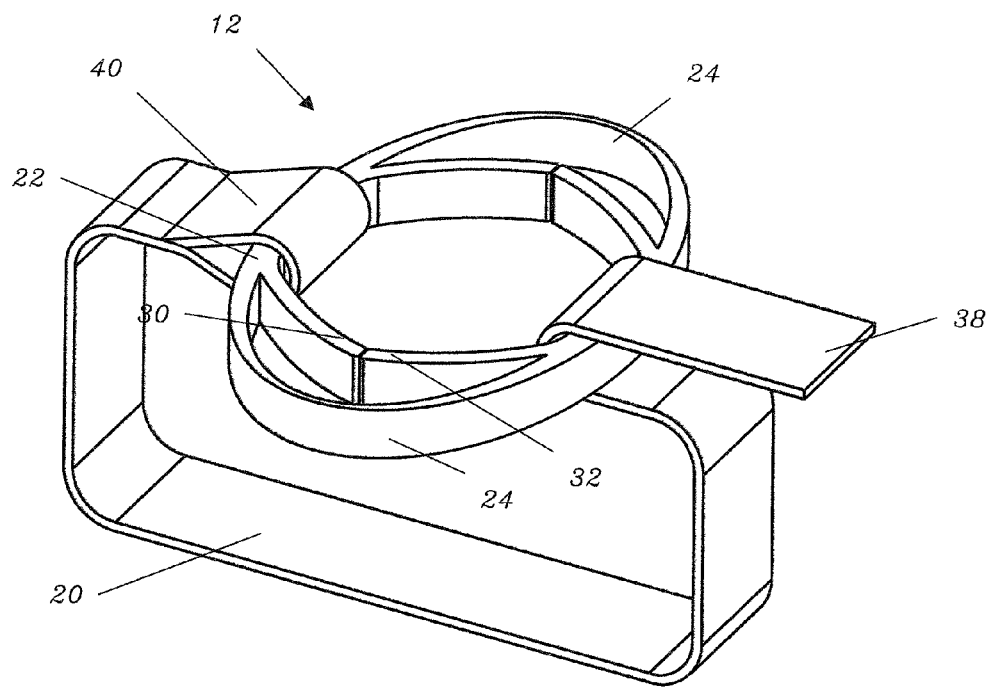
FIG. 2 is an isometric view of the inventive device of FIG. 1 with the bone removed, illustrating the tensioning device of the invention in its untensioned state.
Figure 3:
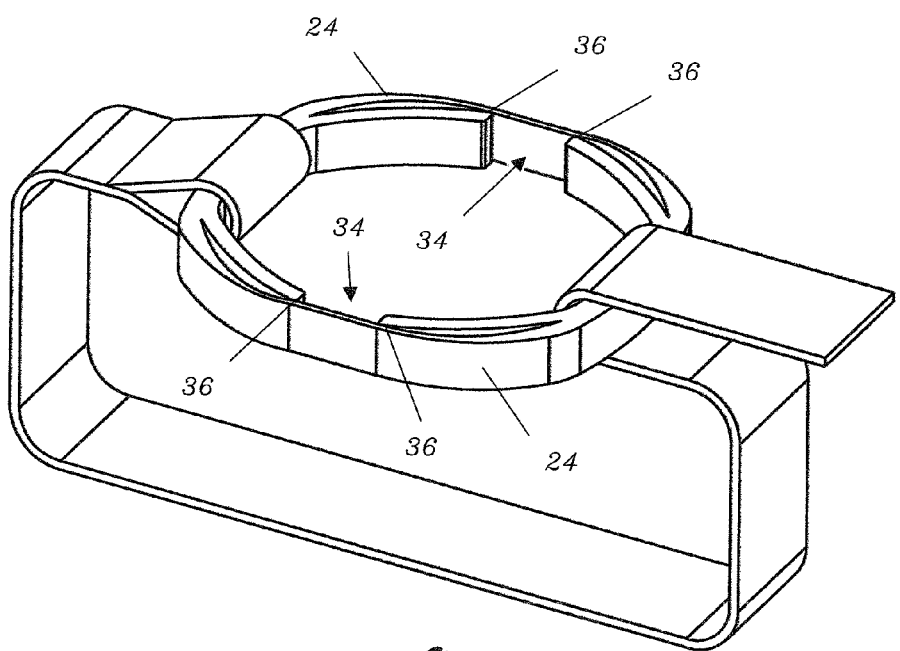
FIG. 3 is an isometric view similar to FIG. 2, illustrating the tensioning device after the suture has been placed in tension.

FIGS. 2 and 3 offer different perspectives of the same invention illustrated in FIG. 1, with the bone removed. FIG. 2 shows tensioning device 12 in its un-tensioned state. Suture 20 is configured for a cerclage procedure in that each end of the suture 20 is connected to the resilient body 22 with a loop provided to go around the tissue. The suture 20 is represented to be of a flat or tape configuration, but could also be oval or round. A suture end 40 is shown to be permanently attached, but could have any sort of attachment. Provisions for attachment that might make use of knots, mechanisms, bonding, or welding might be provided for on the resilient body 22. Similarly, a suture end 38 is shown to have no such provisions for attachment other than potentially a knot. Other provisions for attachment of the suture end 38 may make use of mechanisms, bonding, or welding provided for on the resilient body 22.

Stops 30 and 32 are shown to be in contact with each other, allowing energy to be stored in the springs 24. FIG. 3 shows the result of tensioning on the suture end 38 which pulls on the resilient body 22, causing springs 24 to flex and a gap 34 to be generated between stops 32 and 34. Stops 32 and 34 adjacent to the surface can be seen to come into contact with spring 24 at contact point 36, thus impeding further extension of the springs 24.

Figure 4:
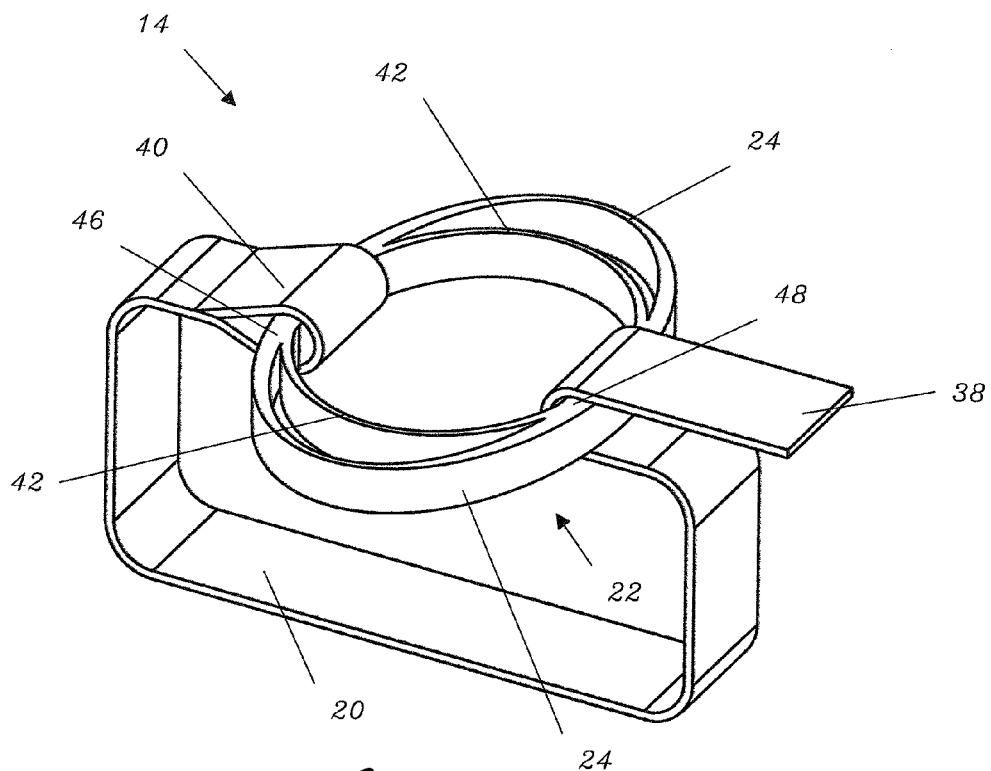
FIG. 4 is an isometric view similar to FIG. 2 of a modified embodiment of the present invention.
Figure 5:
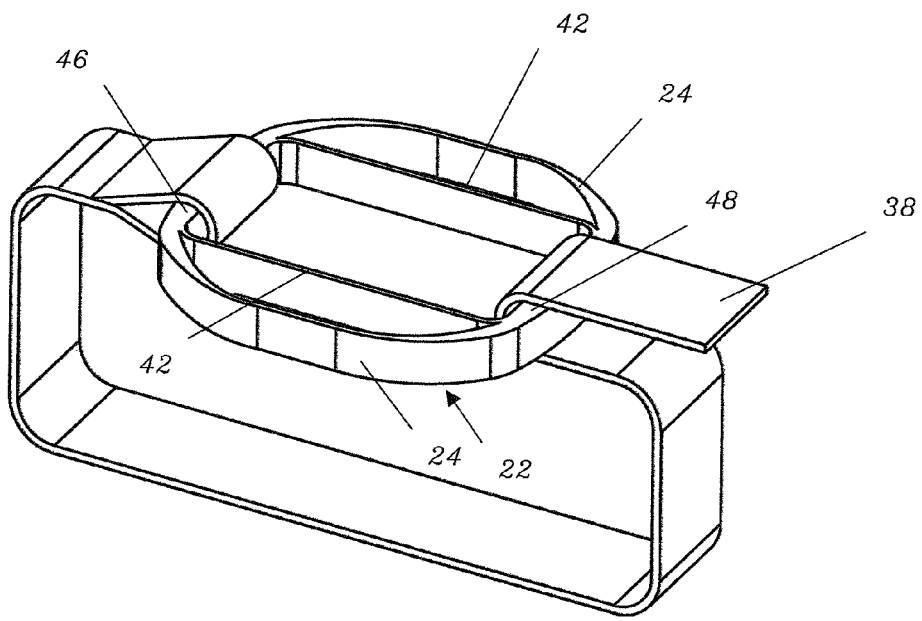
FIG. 5 is an isometric view similar to FIG. 4 of the modified embodiment of FIG. 4, wherein the suture has been placed in tension.

Some tensioning devices may have sufficient tensioning properties without the stop mechanism to manage tension at the end of the healing cycle. But such a tensioning mechanism may still need to protect the spring from damage due to excessive physiologic or native load bearing forces. FIGS. 4 and 5 provide an embodiment of the present invention that allows for such parameters. Instead of having a stop structure interfering with the motion of the spring 24 on the resilient body 22 in the prior embodiment, this embodiment utilizes a strap 42 that is significantly more flexible than the spring 24. The strap 24 has a shorter path length between suture attachment points 46 and 48 than the spring 24. Consequently, as the suture end 38 is pulled to tension the suture 20, the strap 42 will become straight before the spring 24 can hyper-extend, causing damage to its ability to store energy. Thus, the present invention allows the tensioning device 14 to contain excessive physiologic or native load bearing forces without damaging the energy storage capabilities of the spring. Such a strap also keeps the bone fragments 16 and 18 in proximity with one another while these excessive forces are realized.

Figure 6:
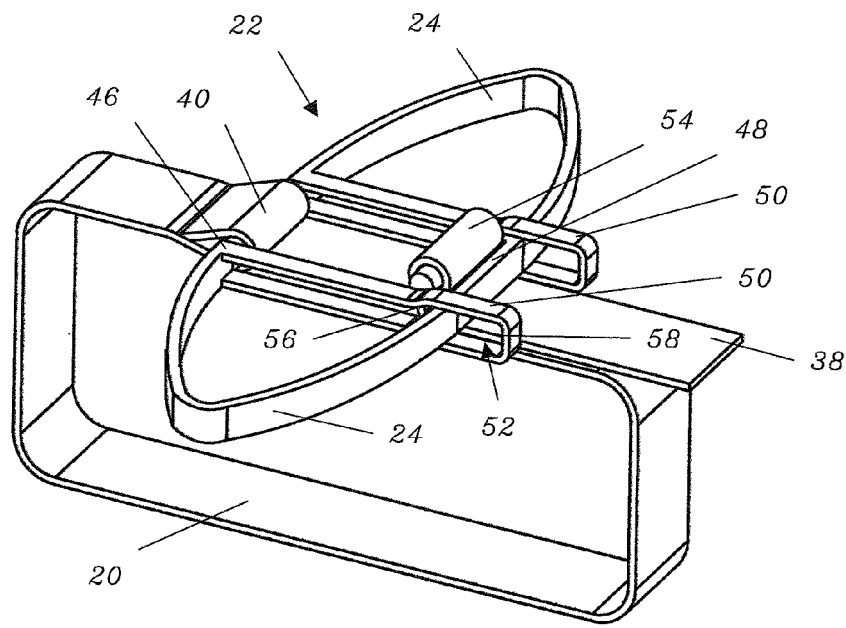
FIG. 6 is an isometric view similar to FIGS. 2 and 4, illustrating still another modified embodiment of the present invention.
Figure 7:
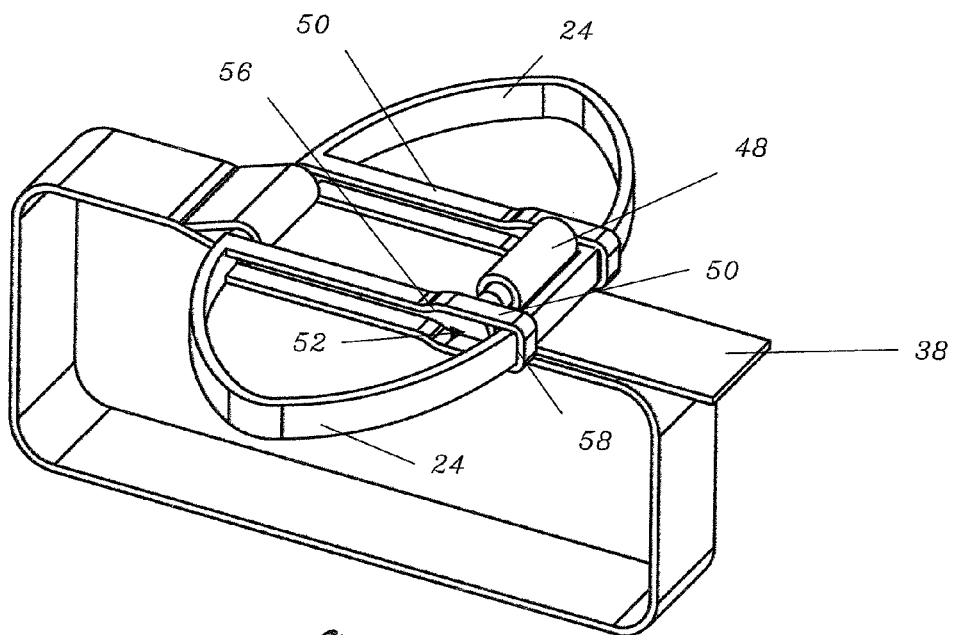
FIG. 7 is an isometric view similar to FIG. 6 of the modified embodiment of FIG. 6, wherein the suture has been placed in tension.

FIGS. 4 and 5 illustrate a modified embodiment of the present invention, which utilizes an internal strap. The configuration of the internal strap has its advantages and its disadvantages. Attachment of the strap to the spring and resilient body can be expensive, especially when it competes for other elements that facilitate the attachment of the suture to the resilient body. It is advantageous, in some respects, to locate the strap externally. FIGS. 6 and 7 illustrate how this is done.

Tensioning device 14 comprises a resilient body 22, springs 24, a strap 50, and suture 20 with suture ends 38 and 40. Stops 58 serve to confine the motion of a suture attachment point 48 on the resilient body 22 within a window 52 provided by strap 50. Springs 24 can be pre-loaded to supply a final healing force by ensuring springs 24 are pushing against window end 56 in window 52. As suture end 38 is pulled to tension resilient body 22, springs 24 extend, allowing the resilient body suture attachment point 48 to move outwardly in window 52, supplied by straps 50. When sufficient movement has been caused by resilient body 22 from the tensioning of strap 38, resilient body suture attachment point 48 contacts the outward surface of window 52 supplied by straps 50. Further tensioning of suture end 38 will not damage spring 24. Moreover, stop 58 (created by strap 50) in window 52 serves to contain physiologic or native load bearing forces without damaging the energy storage capabilities of the spring 24.

It should be noted that, while elements 50 are identified as straps, it is within the scope of the invention for these elements to be either relatively rigid or relatively flexible.

FIGS. 6 and 7 show an embodiment of the present invention that utilizes a buckle 48 to contain tension applied to the suture end 38 during tensioning. Such a buckle imparts significant frictional loads onto the suture when tensioning. These frictional loads are added to the spring 24 during tensioning. These frictional loads are also removed from spring 24 when tension is released from suture end 38. The consequence of this force dynamic is that a lot more force needs to be applied to suture ends 38, which gets transferred directly to springs 24, and could easily damage springs 24 if not for the stop 58 provided by the strap 50. Of further consequence is such a strap 50 is needed for any suture attaching mechanism, such as buckle 54, that contains latent friction during tensioning.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A surgical tensioning device for dynamically holding two tissue portions in contact with one another, the device comprising:
   a resilient body having a plurality of spring elements;
   a plurality of stop members for limiting travel of the spring elements in order to control energy stored or delivered by the spring elements; and
   a length of suture, wherein a first end of the suture is connected to said resilient body at a first attachment point and a second end of the suture is connected to said resilient body at a second attachment point;
   wherein when the suture is placed in tension, the spring elements move to an extended configuration and the stop members move apart, creating gaps between ends of each of the stop members, and further wherein when the gaps become sufficiently large, edges of the stop elements contact corresponding spring elements to impede further widening of the gaps and consequent further extension of the spring elements.

2. The surgical tensioning device as recited in claim 1, wherein the suture comprises flat suture.

3. The surgical tensioning device as recited in claim 1, wherein the spring elements comprise leaf springs.

4. The surgical tensioning device as recited in claim 1, wherein the stop members contact one another to limit compression of the spring elements.

5. The surgical tensioning device as recited in claim 1, wherein the stop elements are formed of a relatively rigid material.

6. The surgical tensioning device as recited in claim 1, wherein the stop elements are formed of a relatively flexible material.

7. The surgical tensioning device as recited in claim 1, wherein the stop elements comprise straps.

8. The surgical tensioning device as recited in claim 7, wherein one of the straps, disposed between the first and second attachment points, is substantially shorter than a corresponding one of said spring elements.

9. The surgical tensioning device as recited in claim 8, wherein the spring elements are prevented from further extension once the straps become fully extended between the first and second attachment points.

10. The surgical tensioning device as recited in claim 9, wherein the straps extend externally to the spring elements, and wherein said straps may be either flexible or rigid.

11. The surgical tensioning device as recited in claim 1, and further comprising a buckle for containing tension applied to at least one of the suture ends during tensioning.

12. A surgical tensioning device for dynamically holding two tissue portions in contact with one another, the device comprising:
   a resilient body having a plurality of spring elements;
   a plurality of stop members, comprising straps, for limiting travel of the spring elements in order to control energy stored or delivered by the spring elements; and
   a length of suture, wherein a first end of the suture is connected to said resilient body at a first attachment point and a second end of the suture is connected to said resilient body at a second attachment point;
   wherein one of the straps, disposed between the first and second attachment points, is substantially shorter than a corresponding one of said spring elements, and the spring elements are prevented from further extension once the straps become fully extended between the first and second attachment points.

13. The surgical tensioning device as recited in claim 12, wherein the straps extend externally to the spring elements, and wherein said straps may be either flexible or rigid.

14. The surgical tensioning device as recited in claim 12, wherein the suture comprises flat suture.

15. The surgical tensioning device as recited in claim 12, wherein the spring elements comprise leaf springs.

16. The surgical tensioning device as recited in claim 12, wherein the stop members contact one another to limit compression of the spring elements.

17. The surgical tensioning device as recited in claim 12, wherein when the suture is placed in tension, the spring elements move to an extended configuration and the stop members move apart, creating gaps between ends of each of the stop members.

18. The surgical tensioning device as recited in claim 17, wherein when the gaps become sufficiently large, edges of the stop elements contact corresponding spring elements to impede further widening of the gaps and consequent further extension of the spring elements.

19. The surgical tensioning device as recited in claim 12, wherein the stop elements are formed of a relatively rigid material.

20. The surgical tensioning device as recited in claim 12, wherein the stop elements are formed of a relatively flexible material.

21. A surgical tensioning device for dynamically holding two tissue portions in contact with one another, the device comprising:
   a resilient body having a plurality of spring elements;
   a plurality of stop members for limiting travel of the spring elements in order to control energy stored or delivered by the spring elements, wherein the stop members contact one another to limit compression of the spring elements; and
   a band having a length, wherein a first end of the band is connected to said resilient body at a first attachment point and a second end of the band is connected to said resilient body at a second attachment point
   wherein the expansion and compression of the spring elements causes the resilient body to change its dimensional form in a direction along said band length
   wherein when the band is placed in tension, the spring elements move to an extended configuration and the stop members move apart, creating gaps between ends of each of the stop members
   wherein when the gaps become sufficiently large, edges of the stop elements contact corresponding spring elements to impede further widening of the gaps and consequent further extension of the spring elements.

22. The surgical tensioning device as recited in claim 21, wherein said band comprises suture.

23. The surgical tensioning device as recited in claim 22, wherein the suture comprises flat suture.

24. The surgical tensioning device as recited in claim 21, wherein the spring elements comprise leaf springs.

25. The surgical tensioning device as recited in claim 21, wherein the stop elements comprise straps.

26. The surgical tensioning device as recited in claim 25, wherein one of the straps, disposed between the first and second attachment points, is substantially shorter than a corresponding one of said spring elements.

27. The surgical tensioning device as recited in claim 26, wherein the spring elements are prevented from further extension once the straps become fully extended between the first and second attachment points.

28. The surgical tensioning device as recited in claim 27, wherein the straps extend externally to the spring elements, and wherein said straps may be either flexible or rigid.

29. The surgical tensioning device as recited in claim 21, and further comprising a buckle for containing tension applied to at least one of the band ends during tensioning.

* * * * *